United States Patent [19]
Salter et al.

[11] Patent Number: 5,133,032
[45] Date of Patent: Jul. 21, 1992

[54] OPTICAL FIBER CONNECTOR

[76] Inventors: James R. Salter, 18 N. Deerfront Cir.; Nadhir B. Kosa, 2 Feather Branch Ct., both of, The Woodlands, Tex. 77380

[21] Appl. No.: 686,779
[22] Filed: Apr. 17, 1991
[51] Int. Cl.⁵ .............................................. G02B 6/38
[52] U.S. Cl. .................................. 385/60; 385/59
[58] Field of Search ............... 350/96.2, 96.21, 96.22

[56] References Cited

U.S. PATENT DOCUMENTS

| | | | |
|---|---|---|---|
| 4,214,812 | 7/1980 | de Mendez | 350/96.21 |
| 4,277,135 | 7/1981 | Schrott et al. | 350/96.21 |
| 4,279,468 | 7/1981 | Turley et al. | 350/96.21 |
| 4,323,300 | 4/1982 | Stewart et al. | 350/96.21 |
| 4,405,201 | 9/1983 | Cefarelli et al. | 350/96.21 |
| 4,611,887 | 9/1986 | Glover et al. | 350/96.21 |
| 4,684,245 | 8/1987 | Goldring | 356/41 |
| 4,697,593 | 10/1987 | Evans et al. | 128/634 |
| 4,759,599 | 7/1988 | Yamaguchi et al. | 350/96.21 |
| 4,778,243 | 10/1988 | Finzel | 350/96.21 |
| 4,779,952 | 10/1988 | Hayashi et al. | 350/96.21 |
| 4,818,059 | 4/1989 | Kakii et al. | 350/96.21 |
| 4,824,204 | 4/1989 | Pafford | 350/96.21 |
| 4,836,638 | 6/1989 | Finzel | 350/96.21 |
| 4,872,736 | 10/1989 | Myers et al. | 350/96.2 |
| 4,911,526 | 3/1990 | Hsu et al. | 350/96.24 |
| 4,960,317 | 10/1990 | Briggs et al. | 350/96.21 |
| 4,989,606 | 2/1991 | Gehrich et al. | 128/637 |
| 5,005,939 | 4/1991 | Arvanitakis | 350/96.2 |
| 5,007,704 | 4/1991 | McCartney | 350/96.21 |
| 5,015,059 | 5/1991 | Booth et al. | 350/96.17 |
| 5,016,968 | 5/1991 | Hammond et al. | 350/96.2 |
| 5,018,316 | 5/1991 | Mulholland et al. | 51/216 |

OTHER PUBLICATIONS

"Amphenol-A World Leader in Interconnects Today and Tomorrow," Amphenol Corporation, Apr., 1989 (portions dated earlier than Apr., 1989); particularly pp. 7–18 of section entitled Amphenol fiber optical designer's handbook; section entitled Multichannel Connectors; and section entitled Multi Mode Couplers.
"Amphenol SMA Connector Termination Procedure," Amphenol Corporation, Jul., 1988.

Primary Examiner—Frank Gonzalez

[57] ABSTRACT

Connector for stable interface of optical fibers, in one aspect having matable body parts with interior fiber mounts, the matable body parts securable together e.g. by one or more retention clips, snap-fit, or one or more screws; and in one aspect, a middle block or bushing bar for increased stability and convenient access to fiber ends.

15 Claims, 3 Drawing Sheets

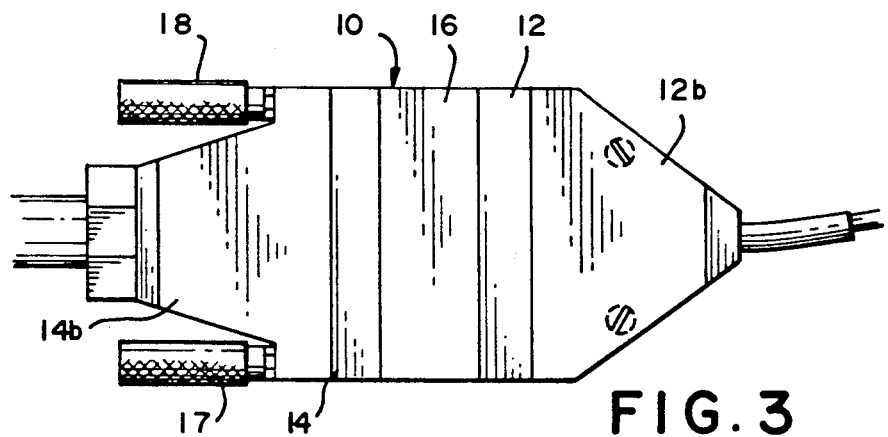
FIG. 3
FIG. 4a
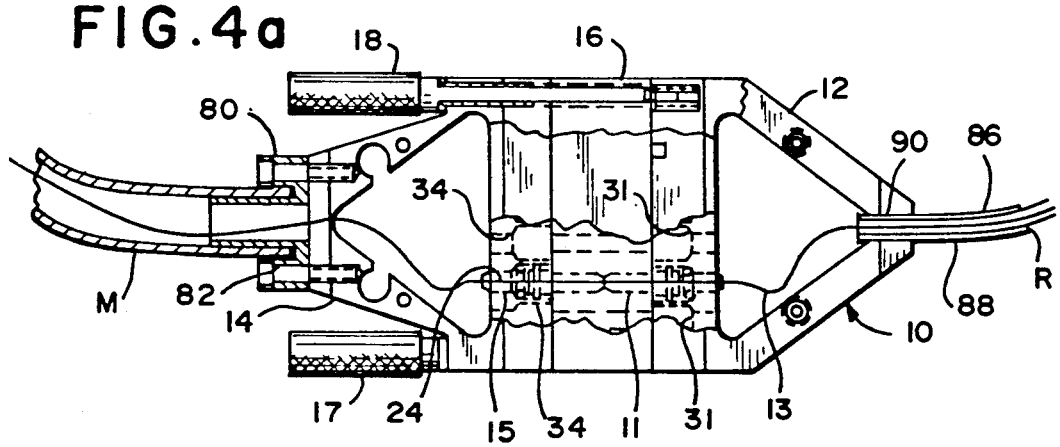
FIG. 4b
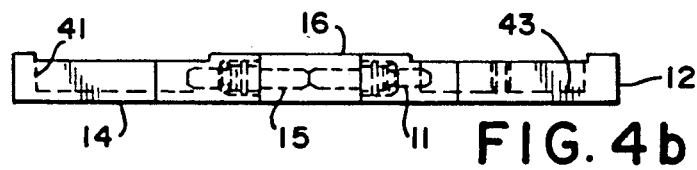
FIG. 5
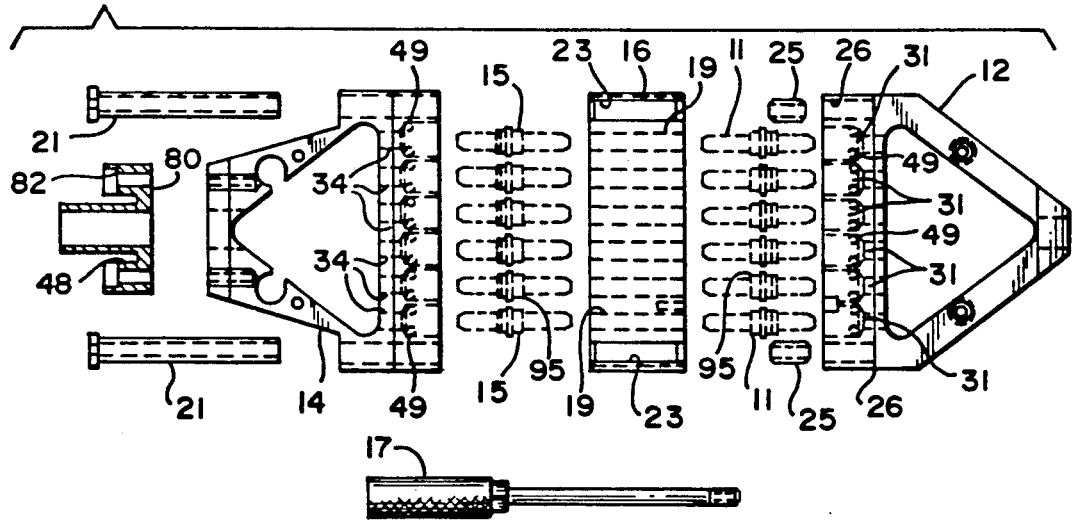

OPTICAL FIBER CONNECTOR

BACKGROUND OF THE INVENTION

1. Field of the Invention

This invention is directed to optical fibers, devices using them, and connectors for such fibers. In certain particular aspects this invention is directed to a connector which provides a stable interface for optical fibers particularly two or more such interfaces.

2. Description of Related Art

An optical signal, e.g. a change in a light ray, conveyed by an optical fiber is an analog (as opposed to a digital) signal. The intensity, amplitude, phase, frequency, pulse width, time of flight, polarization, and wavelength of the light may vary.

In various instruments using optical fibers and sensing materials which due to environmental changes (e.g. changes in heat, pressure, humidity, etc.) or change when contacted by certain chemicals, the change in the sensing materials effects a change in light passing through the sensing materials. For these instruments to produce accurate measurements, i.e. accurate indications of the change, the transmitted light signal should be as unaffected as possible by extraneous influences, particularly over long periods of time. Stability problems are encountered with certain prior art male-female connectors, particularly when frequent plugging and unplugging are required. Also, it is possible for such connectors to be plugged together with the fiber ends somewhat laterally or longitudinally displaced, or non-parallel with respect to each other; at an undesired distance apart; or with their ends rotated with respect to each other at an undesired angle.

Various prior art devices require that an optical fiber sensor interface with some type of near or remote controlling and/or monitoring and/or recording base system. In the past the fiber-fiber interface has lacked stability; i.e., due to the structure of items such as optical fiber mounts and connectors, the fibers have been permitted some degree of freedom of movement or have become skewed in position, resulting in an alteration and degradation of the light ray optical signal being transmitted by the fiber. When the signal conveyed is digital rather than analog, fiber-fiber interface stability is less of a problem. In highly sensitive analog measurements, however, e.g. the measurement of the concentration level of blood gases, even a minimal amount of mount or connector instability can result in degraded or useless measurements.

There has long been a need for a device which provides a stable fiber-fiber interface for optical fibers. There has long been a need for a stable two-part optical-fiber connector. There has long been a need for such a connector which can be used with two or more pairs of interfacing optical fibers. There has long been a need for an optical fiber connector which insures that fiber ends are disposed adjacent each other in a desired relative disposition, and in a desired proximity.

SUMMARY OF THE PRESENT INVENTION

The present invention, in one embodiment, discloses an optical fiber connector that includes: a first part and a second part; the first part having a first body member with one or more optical fibers mounted therein and stabilized therein by mounting in a fiber holder such as a hollow tube, each tube extending from the first body member with an adhesive holding the fiber in place in the tube (e.g. epoxy); the fiber or fibers surrounded by a sheath that enters from another end of the first body member, the sheath (e.g., made from co-extruded polyvinylchloride/ polyethylene); at the sheath opening in the first body member an additional supportive sheath (e.g., of polyvinylchloride) may be used for added protection, strain relief, and stability; the second part having a second body member with a recess or recesses therein corresponding to the hollow tube or tubes of the first body member and mounted in each recess an optical fiber corresponding to each optical fiber mounted in the tube or tubes of the first body member; and apparatus such as a bolt or bolts for securing together the first part and second part for added stability.

The hollow tubes of the first part of the connector serve to isolate two or more fibers from each other. By using opaque tubes, e.g. hollow stainless steel ferrules, and by sheathing each fiber, light in one fiber does not affect light in another fiber. It is preferred that the tubes be hard and/or rigid. Use of a material such as a metal also adds to overall stability. By mounting the hollow tubes or ferrules in holes in the first part and second part with an O-ring in the holes abutting a first shoulder on the ferrule and also abutting a portion of the first part on second part and by properly sizing the holes, free floating of the ferrules in these holes is achieved that permits proper ferrule alignment. Ferrules with a second shoulder for abutting a middle block disposed between the first part and second part are thrust against the middle block, the second shoulder contacting the middle block to provide precise disposition of the ferrules and accurate positioning of the fiber ends that are in the ferrules.

Although retention clips may be used to secure the first and second parts together, or some type of snap-fit structure on the parts, a stable connection can also be achieved with a screw or screws on one part that threadedly engages holes on the other part. Thus the parts are urged and held together so that the mated assembly is substantially inflexible and stable. Although one screw-hole structure provides added stability whether located medially or peripherally of the connector, spaced apart screw pairs located at the edges of the connector are preferred in certain embodiments.

In another embodiment a connector according to the present invention has a first part for receiving and holding one or more first optical fibers, each of the first optical fibers non-rotatably mounted to the first part, a second part for receiving and holding one or more second optical fibers, each of the second optical fibers non-rotatably mounted to the second part, and a connector on the first and second parts for securing them together in non-rotatable relation, an end of each of the first optical fibers adjacent an end of each of the second optical fibers. In one embodiment, the connector has one or more sets of holes, each set including a hole in the first part and a corresponding hole in the second part, with a screw extending through each hole set so that tightening the screw brings the parts securely together. In another embodiment of such a connector, there is a middle block disposed between the first part and the second part with the connector also securing the middle block between the first part and the second part and each of the first optical fibers mounted in the first part with an end protruding therefrom, each of the second optical fibers mounted in the second part with an end protruding therefrom, and the middle block having holes therein for receiving and holding the protruding fiber ends of the first optical fibers in fixed relation to the protruding fiber ends of the second optical fibers.

At least certain embodiments of connectors according to the present invention are stable when subjected to movement, pulling or frequent connection, disconnection, and re-connection; and can be miniaturized while providing multi-fiber interfaces.

It is, therefore, an object of at least certain preferred embodiments of the present invention to provide new, useful, unique, efficient, and effective devices and methods for interfacing the ends of optical fibers.

Another object of at least certain preferred embodiments of the present invention is the provision of such devices and methods which include a stable two-part or multi-part connector for effecting such a fiber-fiber interface.

Yet another object of at least certain preferred embodiments of the present invention is the provision of such methods and devices which can be used to interface one or more optical fibers.

An additional object of at least certain preferred embodiments of the present invention is to effect a very stable fiber-fiber interface in which degradation of the transmitted optical signal is reduced or minimized.

Another object of at least certain preferred embodiments of the present invention is the provision of such devices and methods which include the positive securement of connector pieces for increased stability.

Yet another object of the present invention is the provision of such devices and methods which reduce or minimize the misalignment of adjacent fiber ends and which reduce or minimize unwanted spacing between fiber ends.

The present invention recognizes and addresses the previously-mentioned long-felt needs and provides a satisfactory meeting of those needs in its various possible embodiments. To one of skill in this art who has the benefits of this invention's teachings and disclosures, other and further objects and advantages will be clear, as well as others inherent therein, from the following description of presently-preferred embodiments, given for the purpose of disclosure, when taken in conjunction with the accompanying drawings. Although these descriptions are detailed to insure adequacy and aid understanding, this is not intended to prejudice that purpose of a patent which is to claim an invention no matter how others may later disguise it by variations in form or the addition of further improvements.

Incorporated fully herein for all purposes are U.S. Pat. No. 4,682,895 issued on Jul. 28, 1987 entitled "Fiber Optic Probe For Quantification of Colorimetric Reactions" and pending U.S. Application Ser. No. 07/526,822 filed on May 22, 1990 entitled "Optical Probe," copies of which are submitted with the application for this patent.

DESCRIPTION OF THE DRAWINGS

So that the manner in which the above-recited features, advantages and objects of the invention, as well as others which will become clear, are attained and can be understood in detail, more particular description of the invention briefly summarized above may be had by reference to certain embodiments thereof which are illustrated in the appended drawings, which drawings form a part of this specification. It is to be noted, however, that the appended drawings illustrate preferred embodiments of the invention and are therefore not to be considered limiting of its scope, for the invention may admit to other equally effective equivalent embodiments.

FIG. 3 is a top view of the connector of FIG. 2.

FIG. 4a is a cutaway view of the connector of FIG. 3. FIG. 4b is a side cross-sectional view of the connector of FIG. 4a.

FIG. 5 is an exploded view of the connector of FIG. 3 showing one of the two knurled screws.

DESCRIPTION OF EMBODIMENTS PREFERRED AT THE TIME OF FILING FOR THIS PATENT

Figure 1:
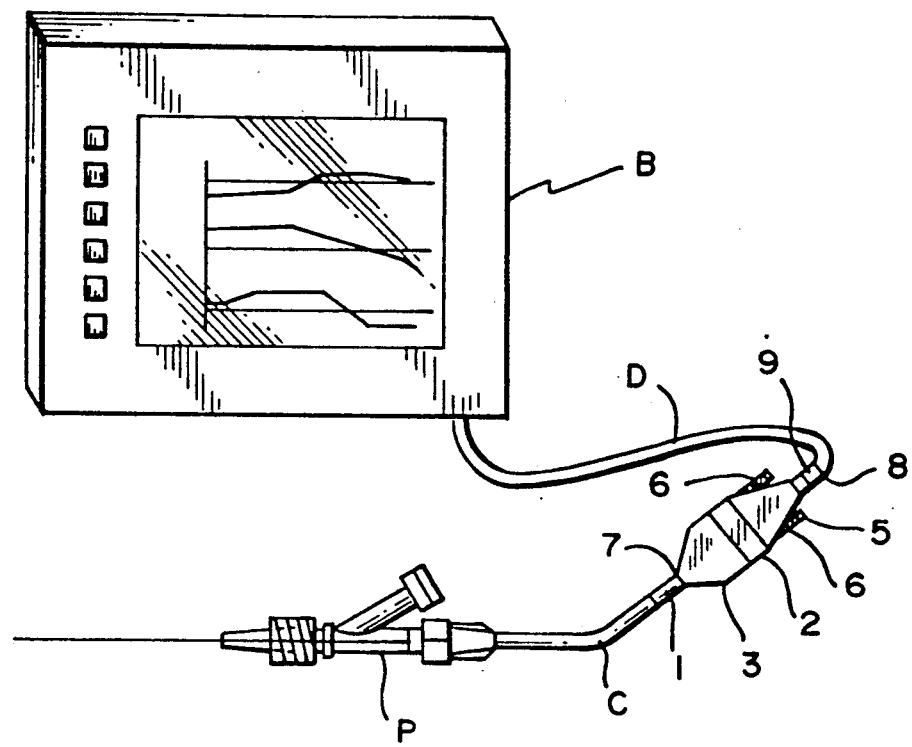
FIG. 1 is a perspective view of a system with a connector according to the present invention.

Referring now to FIG 1, a fiber optic probe P is interconnected with a base system B with a multi-fiber connector 2 according to the present invention. The base system B generates an original light ray or rays, receives and measures a change in the analog light signal from the probe P, records the signal, and continuously displays an indication of the signal value. A multi-fiber cable C extends from the probe P to a male part 3 of the connector 2. For example, the cable C may contain six optical fibers in a probe that is about 700 microns in diameter. A tether cable D extends from the female part 5 to the base system B and contains an optical fiber (not shown) corresponding to each optical fiber (not shown) 4 of the male part 3. Knurled screws 6 extend through openings (not shown) in the female part 5 and engage threaded holes (not shown) in the male part 3 to further stabilize the connector 2. At openings 7, 8 of the parts 3, 5, respectively, a sheath 1,9 respectively protects the respective cable and provides additional stability and also strain relief.

Figure 2:
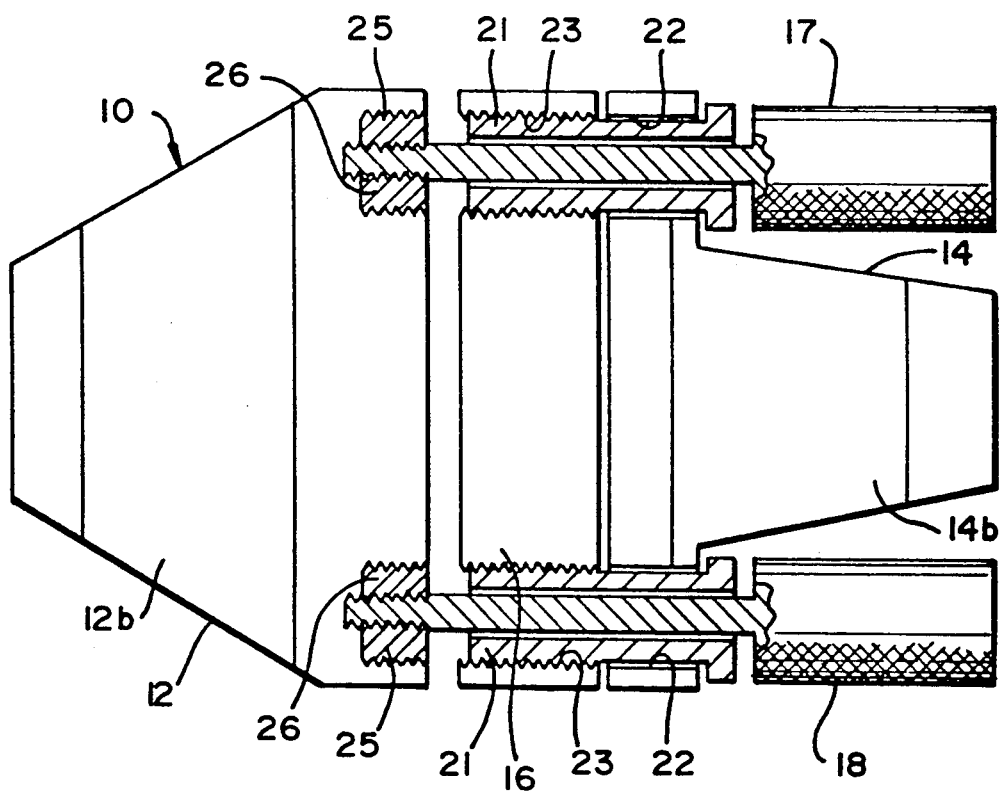
FIG. 2 is a top view of a connector according to the present invention.

Referring now to FIG. 2, a connector 10 according to the present invention has a male part 12 and a female part 14, with a bushing bar 16 which is securable to the female part 14 with knurled screws 17, 18 which pass through threaded sleeves 21 in holes 22 in the female part 14, and through the threaded sleeves that extend further through holes 23 in the bushing bar 16, and enter into and engage threaded inserts 25 in holes 26 in the male part 12. For illustration the pieces are shown spaced apart; but tightening the screws brings the parts into contact and stabilizes the connector as shown in FIG. 3. So that the connector is stable when it is moved or pulled while still connected and, after disconnection, upon reconnection so that pairs of fiber ends (one in a male part and a corresponding fiber end in a female part) are positioned and aligned with each other substantially as they were prior to disconnection.

As shown in FIG. 4a and FIG. 5, the male part 12 has a series of holes 31 in which are mounted stainless steel ferrules 11. A single optical fiber 13 is mounted in each ferrule. The fiber extends from the male part 12 to an optical sensor (not shown). Similarly, stainless steel ferrules 15 are mounted in holes 34 in the female part 14 and an optical fiber 24 is mounted in each ferrule which extends to a base system (e.g. like system B, FIG. 1) and which corresponds to one of the optical fibers in the male part 12. Thus, interfaced and aligned optical fiber pairs are provided so that a signal from the probe is conveyed through the connector 10 to the base system.

FIG. 4b shows a side cutaway view of the connector of FIG. 4a and illustrates a recess 41 in the female part 14 and a recess 43 in the male part 12. These recesses provide access to the parts' interiors and permit access to the ferrules.

The bushing bar 16 has a series of holes 19 through which the stainless steel ferrules of parts 12 and 14 pass. O-rings 49 (one in each hole 34, 31) assist in ferrule positioning.

As shown in FIG. 4a and FIG. 5, a cable M leads from the connector 10 to a base system (not shown) which may have a light source from which some optical fibers lead and a light detector to which other optical fibers lead. For added stability, an end of the cable end is received in a recess 48 of a cable mount 80. Screws (not shown) enter through holes 82 and into holes 84 of the female part 14 to connect the mount 80 to the female part 14. A support sheath 86 surrounds an end 88 of a cable R that leads from an opening 90 in the connector 10 to a sensor and which protects the optical fibers therein.

Figure 6:
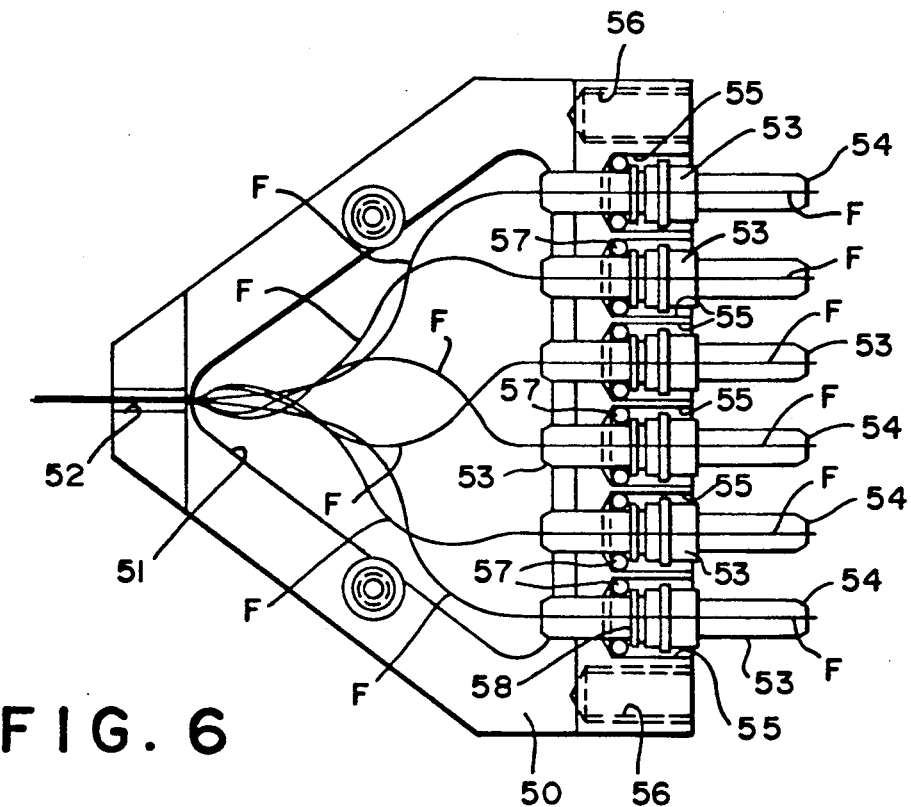
FIG. 6 is a top view of a connector according to the present invention, partially in cross-section.

FIG. 6 illustrates a male part 50 according to the present invention (like the male part shown in FIGS. 3) with a recess 51 with its cover plate removed to reveal six optical fibers F entering through a hole 52 and leading to stainless steel ferrules 53. An end of each fiber F extends to an end 54 of each ferrule and is held in place within the ferrule by epoxy adhesive. The ferrules are held in holes 55 by an elastomeric bushing 57 (e.g., an O-ring) with a friction fit. Threaded holes 56 engag a threaded bolt (not shown) to secure the male part 50 to a female part (not shown). Fibers are similarly mounted in ferrules in a female part.

The O-rings 57 (and 4a, FIG. 5) act as elastomer springs which are biased against an inner edge of the holes 55 and against a shoulder 58 on each ferrule to effect a free floating mounting of the ferrules in the holes in the male and female parts. Ferrules on the female part have this same O-ring-shoulder structure and function. The free floating aspect of the ferrules in these holes lets each ferrule self-align in its hole in axial position, angular position and lateral spacing between adjacent ferrules. The thrusting of each ferrule against the bushing bar and the holding of an end of each ferrule in the bushing barin a close fit (due to precise machining and a quality slick finish on the bar and ferrule surfaces) provides axial registration of the fiber end face and precise axial positioning of ferrule pairs (one in the male part, one in the female part) and insures a desired gap between fiber ends or a desired contact point. The ferrules are not free to rotate in their holes and this contributes to reconnection signal continuity.

Although a bushing bar or middle block is not necessary according to the present invention, it is preferred since it can be removed to provide access to the fiber ends in each ferrule (e.g. for polishing). Also, the bar can be precision machined and maintained with the part connected to a base system permitting the other part (e.g. a male part) to be made with less precision. This is valuable when the other part is to be disposable. There is a close fit between the bushing bar holes and the ferrules therein, i.e. the ferrules are not free floating in the bushing bar.

A system according to this invention has a sensor with one or more optical fiber sensors which lead to a male part as previously described (e.g. six 125 micron diameter fibers). Six corresponding optical fibers in a female part are each preferably of a larger diameter, e.g. 230 micron diameter fibers. This type of stepped diameter fiber interface increases connector (e.g. male part plus female part; or male part plus female part plus middle bar) stability. The larger diameter fibers receive most of the light being conveyed to the ends of the smaller diameter fibers; i.e., very little of this light is lost. Some of the larger diameter fibers are connected to a light source in a base system while others are connected to a light detector in the base system. It is also preferred that: the fibers in the probe that receive light from a light source are larger in diameter than the fibers from the light source that transmit light to the fibers of the probe; and that in both the connector and the probe that fibers receiving a light ray from another fiber have a larger numerical aperture than the other fiber.

Figure 7:
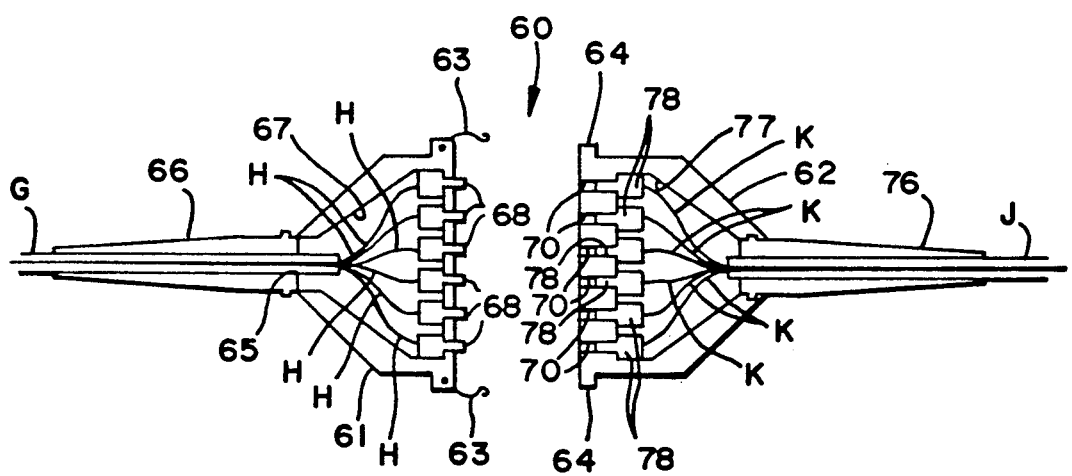
FIG. 7 is a cross-sectional view of a connector according to the present invention.

As illustrated in FIG. 7, a connector 60 according to the present invention has a male part 61 and a female part 62. Two retention clips 63 on the male part 61 engage lips 64 on the female part 62. An optical cable G with a plurality of optical fibers H extends through an opening 65 in the male part 61. A sheath 66 (e.g., made from an elastomer) is secured to the male part 61 and surrounds a portion of the cable G. Each of the fibers H extends through a recess 67 to a stainless steel ferrule 68. The ferrules 68 are mounted in the male part 61 and an end of each fiber is mounted in each ferrule for positioning opposite corresponding fibers in the female part 62.

The female part 62 has a recess 70 for receiving each ferrule 68. An optical cable J with a plurality of optical fibers K extends through an opening 75 in the female part 62. A sheath 76 is partially securably mounted in the female part 62 and surrounds a portion of the cable J. Each of the fibers K extends through a recess 77 to a stainless steel ferrule 78. The ferrules 78 are preferably mounted so that upon connection of the two parts 61, 62 the ferrules 68 of the male part 61 are spaced apart from the ferrules 78 of the female part 62 (e.g., with a gap of about 0.001 inches) and the ends of the fibers H are properly aligned with the ends of the fibers K. Of course, it is within the scope of this invention to provide a connector in which the gap is larger or one in which there is no gap (i.e., the fiber ends are in contact).

In conclusion, therefore, it is seen that the present invention and the embodiments disclosed herein are well adapted to carry out the objectives and obtain the ends set forth at the outset. Certain changes can be made in the method and apparatus without departing from the spirit and the scope of this invention. It is realized that changes are possible and it is further intended that each element or step recited in any of the following claims is to be understood as referring to all equivalent elements or steps for accomplishing substantially the same results in substantially the same or equivalent manner. It is intended to cover the invention broadly in whatever form its principles may be utilized. The present invention is, therefore, well adapted to carry out the objects and obtain the ends and advantages mentioned, as well as others inherent therein.

What is claimed is:

1. A connector for optical fibers, the connector comprising
   a first part for receiving and holding at least one first optical fiber, each of the at least one first optical fiber non-rotatably mounted to the first part,
   a second part for receiving and holding at least one second optical fiber, each of the at least one second optical fiber non-rotatably mounted to the second part, connection means on the first and second parts for securing them together in non-rotatable relation, an end of each of the at least one first optical fiber adjacent an end of each of the at least one second optical fibers, the connection means comprising
- at least one threaded hole in the first part,
  - a hole in the second part corresponding to each of the at least one threaded hole in the first part, and
  - a threaded screw that passes through each of the holes in the second part and threadedly engages the at least one threaded hole in the first part so that tightening of the screw brings the two parts together.

2. The connector of claim 1 wherein
the at least one first optical fiber comprises a plurality of two or more first optical fibers, and
the at least one second optical fiber comprises a plurality of two or more second optical fibers and one second optical fiber corresponds to each of the first optical fibers.

3. The connector of claim 1 wherein
the at least one first optical fiber is smaller in diameter than the at least one second optical fiber.

4. The connector of claim 1 wherein each optical fiber has an end portion securely mounted within a hollow ferrule, each ferrule securely mounted in the first part or the second part.

5. The connector of claim 1 wherein
an end of ferrules of the first part protrude beyond the first part, and
the second part has a recess therein for receiving the end of the ferrules protruding from the first part so that upon such reception the optical fibers of the first part are aligned with the optical fibers of the second part.

6. The connector of claim 1 wherein
there are at least two screws and a hole corresponding to each of the two screws, the two screws spaced apart and positioned at opposite sides of the connector.

7. The connector of claim 1 wherein
a first recess is provided in the first part providing access to the optical fibers therein,
a first cover is removably secured over the first recess,
a second recess is provided in the second part providing access to the optical fibers therein, and
a second cover is removably secured over the second recess.

8. The connector of claim 1 wherein the at least one first optical fiber extends through an opening into the first part and a sheath extends through the opening and surrounds and supports the at least one first optical fiber extending therethrough, and
the at least one second optical fiber extends through a second opening in the second part and a sheath extends through the second opening and surrounds and supports the at least one second optical fiber extending therethrough.

9. The connector of claim 1 comprising also
a middle block disposed between the first part and the second part,
the connection means also securing the middle block between the first part and the second part,
each of the first optical fibers mounted in the first part with an end protruding therefrom,
each of the second optical fibers mounted in the second part with an end protruding therefrom, and
the middle block having holes therein for receiving and holding the protruding fiber ends of the first optical fibers in fixed relation to the protruding fiber ends of the second optical fibers.

10. The connector of claim 9 wherein
the connection means comprises at least one threaded hole in the first part,
a hole in the second part corresponding to each of the at least one threaded hole in the first part,
a hole in the middle block corresponding to each of the at least one threaded hole in the first part, and
a threaded screw that passes through each of the holes in the second part, through each of the holes in the middle block, and threadedly engages the at least one threaded hole in the first part so that tightening of the screw brings the block and the two parts together.

11. The connector of claim 10 wherein
there are two threaded screws, the first holes in the first part, two corresponding block holes in the middle block, and two corresponding second holes in the second part forming two spaced-apart sets of first holes and second holes, a screw passing through each set of holes to hold the first part, second part and middle block together.

12. The connector of claim 9 wherein
each optical fiber has an end portion securely mounted in a hollow ferrule,
each hollow ferrule securely mounted in its corresponding first part or second part,
each hollow ferrule having a first shoulder,
an O-ring disposed about each ferrule and abutting one portion of each O-ring, the first shoulder of the ferrule and another portion of the O-ring abutting a portion of either the first part or of the second part,
the holes of the first part or the second part sized to permit free floating therein of the ferrules.

13. The connector of claim 9 wherein
each ferrule has a second shoulder for contacting a portion of the middle block,
the O-rings thrusting the second shoulders against the portion of the middle block for precise disposition of the ferrules and accurate positioning of the fiber ends therein.

14. A connector for optical fibers, the connector comprising
a first part for receiving and holding a plurality of first optical fibers, each of the first optical fibers non-rotatably mounted in a hollow ferrule securely mounted to the first part,
a second part for receiving and holding a plurality of second optical fibers, each of the second optical fibers non-rotatably mounted in a hollow ferrule securely mounted to the second part,
connection means on the first and second parts for securing them together in non-rotatable relation, an end of each of the at least one first optical fiber adjacent an end of each of the at least one second optical fibers,
the connection means comprising two threaded holes in the first part, the holes spaced apart and on opposite sides of the first part, two holes in the second part, one of the holes corresponding to each of the holes in the first part, and two threaded screws, one of said screws passing through each of the holes in the second part and threadedly engaging the corresponding hole in the first part so that tightening of the screw brings the two parts together.

15. A connector for optical fibers, the connector comprising
- a first part for receiving and holding at least one first optical fiber, each of the at least one first optical fiber non-rotatably mounted to the first part,
- a second part for receiving and holding at least one second optical fiber, each of the at least one second optical fiber non-rotatably mounted to the second part,
- connection means on the first and second parts for securing them together in non-rotatable relation, an end of each of the at least one first optical fiber adjacent an end of each of the at least one second optical fibers,
- a middle block disposed between the first part and the second part,
- the connection means also securing the middle block between the first part and the second part,
- each of the first optical fibers mounted in the first part with an end protruding therefrom,
- each of the second optical fibers mounted in the second part with an end protruding therefrom,
- the middle block having holes therein for receiving and holding the protruding fiber ends of the first optical fibers in fixed relation to the protruding fiber ends of the second optical fibers,
- the connection means comprising two threaded screws, the first holes in the first part, two corresponding block holes in the middle block, and two corresponding second holes in the second part forming two spaced-apart sets of first, block and second holes, a screw passing through each set of holes to hold the first part, second part and middle block together,
- each optical fiber having a end portion securely mounted in a hollow ferrule,
- each hollow ferrule securely mounted in its corresponding first part or second part,
- each hollow ferrule having a first shoulder,
- an O-ring disposed about each ferrule and abutting one portion of each O-ring, the first shoulder of the ferrule and another portion of the O-ring abutting a portion of either the first part or of the second part,
- the holes of the first part and the second part sized to permit free floating therein of the ferrules,
- each ferrule having a second shoulder for contacting a portion of the middle block, and
- the O-rings thrusting the second shoulders against the portion of the middle block for precise disposition of the ferrules and accurate positioning of the fiber ends therein.

* * * * *